United States Patent
Jang et al.

(10) Patent No.: US 8,388,534 B2
(45) Date of Patent: Mar. 5, 2013

(54) APPARATUS FOR PROVIDING SKIN CARE INFORMATION BY MEASURING SKIN MOISTURE CONTENT AND METHOD AND MEDIUM FOR THE SAME

(75) Inventors: Woo Young Jang, Seoul (KR); Kun Soo Shin, Seongnam-si (KR); Hong Sig Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1131 days.

(21) Appl. No.: 11/902,644

(22) Filed: Sep. 24, 2007

(65) Prior Publication Data
US 2008/0091091 A1    Apr. 17, 2008

(30) Foreign Application Priority Data
Oct. 11, 2006 (KR) .................. 10-2006-0098842
Mar. 5, 2007 (KR) .................. 10-2007-0021509

(51) Int. Cl.
*A61B 5/00* (2006.01)
*A61B 5/05* (2006.01)

(52) U.S. Cl. .................. 600/306; 600/346; 600/547
(58) Field of Classification Search .......... 600/306, 600/345, 346, 554, 307
See application file for complete search history.

(56) References Cited

U.S. PATENT DOCUMENTS

| | | | |
|---|---|---|---|
| 4,013,065 A | 3/1977 | Copeland et al. | |
| 4,190,056 A | 2/1980 | Tapper et al. | |
| 4,480,921 A | 11/1984 | Leveque et al. | |
| 4,483,619 A | 11/1984 | Leveque et al. | |
| 4,711,244 A | 12/1987 | Kuzara | |
| 4,956,591 A * | 9/1990 | Schierbeek et al. | 318/483 |
| 4,966,158 A * | 10/1990 | Honma et al. | 600/547 |
| 5,304,112 A * | 4/1994 | Mrklas et al. | 600/27 |
| 5,353,802 A | 10/1994 | Ollmar | |
| 5,738,107 A * | 4/1998 | Martinsen et al. | 600/547 |
| 5,795,293 A | 8/1998 | Carim et al. | |
| 5,944,661 A | 8/1999 | Swette et al. | |
| 6,032,060 A | 2/2000 | Carim et al. | |

(Continued)

FOREIGN PATENT DOCUMENTS

| | | |
|---|---|---|
| JP | 6-66619 | 3/1994 |
| JP | 08-056907 | 3/1996 |

(Continued)

OTHER PUBLICATIONS

Extended European Search Report, mailed Jan. 21, 2008 and issued in corresponding European Patent Application No. 07114519.7-2319.

(Continued)

*Primary Examiner* — Navin Natnithithadha
*Assistant Examiner* — Michael R Bloch
(74) *Attorney, Agent, or Firm* — Staas & Halsey LLP (57) ABSTRACT

An apparatus for providing skin care information, the apparatus including: an electrode unit supplying a voltage to a user's skin and detecting a current signal in the user's skin; a measurement control unit measuring the user's skin moisture content and sweat gland activity by using the detected current signal; a data calculation unit deriving skin moisture content information by using the skin moisture content and the sweat gland activity, and generating skin care information corresponding to the skin moisture content information; and an information provider providing the user with the generated skin care information is provided.

21 Claims, 5 Drawing Sheets

U.S. PATENT DOCUMENTS

| | | |
|---|---|---|
| 6,119,038 A | 9/2000 | Cook |
| 6,289,238 B1 * | 9/2001 | Besson et al. ................ 600/509 |
| 6,326,160 B1 * | 12/2001 | Dunn et al. .................... 435/14 |
| 6,442,422 B1 | 8/2002 | Duckert |
| 6,571,124 B1 * | 5/2003 | Storm .......................... 600/547 |
| 7,753,846 B2 | 7/2010 | Park et al. |
| 8,273,021 B2 | 9/2012 | Jang et al. |
| 2002/0099282 A1 * | 7/2002 | Knobbe et al. ............... 600/365 |
| 2003/0214311 A1 * | 11/2003 | Alanen et al. ................ 324/686 |
| 2003/0222662 A1 | 12/2003 | Geisel |
| 2005/0070778 A1 * | 3/2005 | Lackey et al. ............... 600/366 |
| 2005/0159655 A1 | 7/2005 | Kao |
| 2008/0051643 A1 | 2/2008 | Park et al. |
| 2008/0091091 A1 | 4/2008 | Jang et al. |
| 2008/0177198 A1 | 7/2008 | Jang et al. |

FOREIGN PATENT DOCUMENTS

| | | |
|---|---|---|
| JP | 9-75316 | 3/1997 |
| JP | 10-57322 | 3/1998 |
| JP | 2001-212101 | 8/2001 |
| JP | 2002-90298 | 3/2002 |
| JP | 2003-169788 | 6/2003 |
| JP | 2004-312486 | 11/2004 |
| JP | 2005-52227 | 3/2005 |
| WO | 03/094724 | 11/2003 |

OTHER PUBLICATIONS

Office Action mailed Oct. 29, 2009 in U.S. Appl. No. 11/892,428.
Notice of Allowance mailed Apr. 5, 2010 in U.S. Appl. No. 11/892,428.
Office Action mailed May 26, 2011 in U.S. Appl. No. 11/889,188.
Office Action mailed Dec. 22, 2011 in U.S. Appl. No. 11/889,188.
Notice of Allowance mailed Jun. 7, 2012 in U.S. Appl. No. 11/889,188.

* cited by examiner

(12) United States Patent
US 8,388,534 B2

APPARATUS FOR PROVIDING SKIN CARE INFORMATION BY MEASURING SKIN MOISTURE CONTENT AND METHOD AND MEDIUM FOR THE SAME

CROSS-REFERENCE TO RELATED APPLICATIONS

This application claims the priority benefit of Korean Patent Application No. 10-2006-0098842, filed on Oct. 11, 2006, and Korean Patent Application No. 10-2007-0021509, filed on Mar. 5, 2007, in the Korean Intellectual Property Office, the disclosure of which is incorporated herein by reference.

BACKGROUND

1. Field

Embodiments relate to a method, apparatus, and medium for providing skin care information, and more particularly, to a method, apparatus, and medium for providing skin care information, which can provide a user with more accurate skin care information via skin moisture content excluding a sweat gland activity by measuring an activity of a sweat gland corresponding to a sweat path when measuring the skin moisture content in a stratum corneum, and thereby estimating stress or an effect when the sweat gland activity affects the skin moisture content, and calculating the skin moisture content.

2. Description of the Related Art

As many people become interested in beauty, an interest in skin care has also increased. A desire for a healthy skin affects not only beauty-related businesses, but also affects the growth of medical-related businesses since people need to protect their skin from ultraviolet rays that have become stronger due to the destruction of the ozone layer, and various types of pollutions.

Skin is an organ of the integumentary system made up of multiple layers of epithelial tissues. Main functions of skin are protecting against pathogens, waterproofing, temperature regulation, insulation, and the like. One of the most critical elements to enable the proper performance of the functions of skin is moisture content in a stratum corneum. The moisture content in the stratum corneum is generally called a skin moisture content. When maintaining a particular moisture content in the stratum corneum, it is possible to perform basic functions of skin such as protecting against harmful substances like pathogens, and preventing excessive evaporation of skin moisture. In view of skin care, the skin moisture content is also considered as an essential element. Accordingly, fundamental to skin care is skin moisture management.

According to a conventional art, an electrical measurement method, an optical measurement method, and a method using a magnetic resonance imaging (MRI) are included in a method of measuring skin moisture content. The electrical measurement method is widely used. More specifically, a method of measuring the skin moisture content by measuring susceptance, i.e. an alternating current (AC) component of admittance, of three electrodes using a sinusoidal wave of low frequency is generally used.

Although each skin portion has a different density, a sweat gland corresponding to a sweat path exists in the stratum corneum. Since the sweat gland contains a great amount of moisture, the sweat gland may affect the measurement of the skin moisture content. Thus, an apparatus for providing skin care information, which can reduce an effect of a sweat gland wherever skin moisture content is measured and which can accurately measure skin moisture content in only a stratum corneum when measuring the skin moisture content to provide a user with the user's skin state, is required.

SUMMARY

According to an aspect, there is provided a method and apparatus for providing skin care information, which can simultaneously measure skin moisture content and a sweat gland activity in a stratum corneum, calculate a correlation between the skin moisture content and the sweat gland activity in the stratum corneum, and generate a user's skin care information based on the calculated correlation, and thereby can provide the user with the generated skin care information.

According to an aspect, there is provided a method and apparatus for providing skin care information, which can measure a user's sweat gland activity in the user skin when an external stimulus is applied to the user skin, calculate the user's stress level, generate skin care information based on the user's stress by using the stress level and skin moisture content, and thereby provide the generated skin care information.

According to an aspect, there is provided an apparatus for providing skin care information, the apparatus including: an electrode unit to supply a voltage to a user's skin and to detect a current signal in the user's skin; a measurement control unit to measure the user's skin moisture content and sweat gland activity by using the detected current signal; a data calculation unit to derive skin moisture content information by using the skin moisture content and the sweat gland activity, and to generate skin care information corresponding to the skin moisture content information; and an information provider to provide the user with the generated skin care information.

According to another aspect, there is provided a method of providing skin care information, the method including: supplying a voltage to a user's skin, and detecting a current signal in the user's skin; measuring the user's skin moisture content and sweat gland activity by using the current signal; deriving skin moisture content information by using the skin moisture content and the sweat gland activity; generating skin care information corresponding to the skin moisture content information; and providing the user with the generated skin care information.

According to another aspect, there is provided at least one computer readable medium storing computer readable instructions that control at least one processor to implement a method for providing skin care information, the method including: supplying a voltage to a user's skin, and detecting a current signal in the user's skin; measuring the user's skin moisture content and sweat gland activity by using the current signal; deriving skin moisture content information by using the skin moisture content and the sweat gland activity; generating skin care information corresponding to the skin moisture content information; and providing the user with the generated skin care information.

An apparatus for providing skin care information according to a measurement of skin moisture content according to an aspect may be embodied as any portable device, such as a mobile communication terminal, a personal digital assistance (PDA), a portable game device, an Moving Picture Experts Group Audio-Layer 3 (MP3) player, a portable multimedia player (PMP), a Digital Multimedia Broadcasting (DMB) terminal, a notebook, and the like. The apparatus for measuring skin moisture content may be embodied as a partial configuration of the portable devices or may be independently embodied as a single product, instead of being embodied as the partial configuration of the portable devices.

BRIEF DESCRIPTION OF THE DRAWINGS

These and/or other aspects, features, and advantages will become apparent and more readily appreciated from the following description of exemplary embodiments, taken in conjunction with the accompanying drawings of which.

DETAILED DESCRIPTION OF EMBODIMENTS

Reference will now be made in detail to exemplary embodiments, examples of which are illustrated in the accompanying drawings, wherein like reference numerals refer to the like elements throughout. Exemplary embodiments are described below by referring to the figures.

Figure 1:
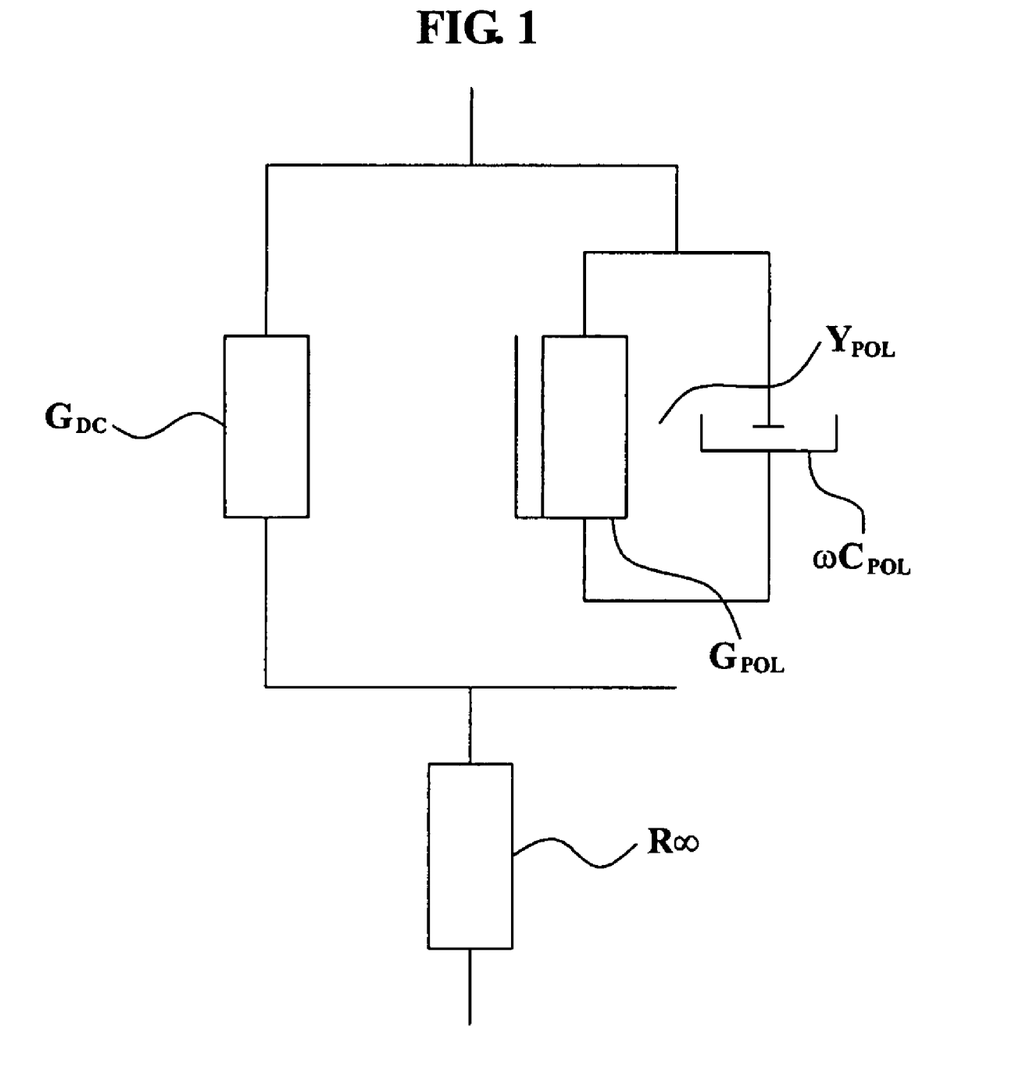
FIG. 1 is a circuit diagram illustrating an electrically modeled biological structure of skin.

FIG. 1 is a circuit diagram illustrating an electrically modeled biological structure of skin.

Figure 2:
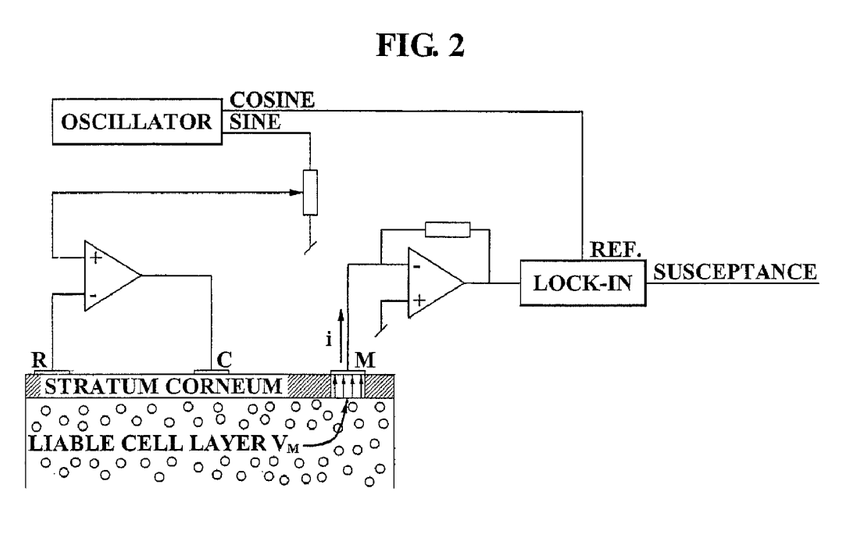
FIG. 2 is a diagram illustrating a measurement principle of measuring skin moisture content.

FIG. 2 is a diagram illustrating a measurement principle of measuring skin moisture content.

Figure 3:
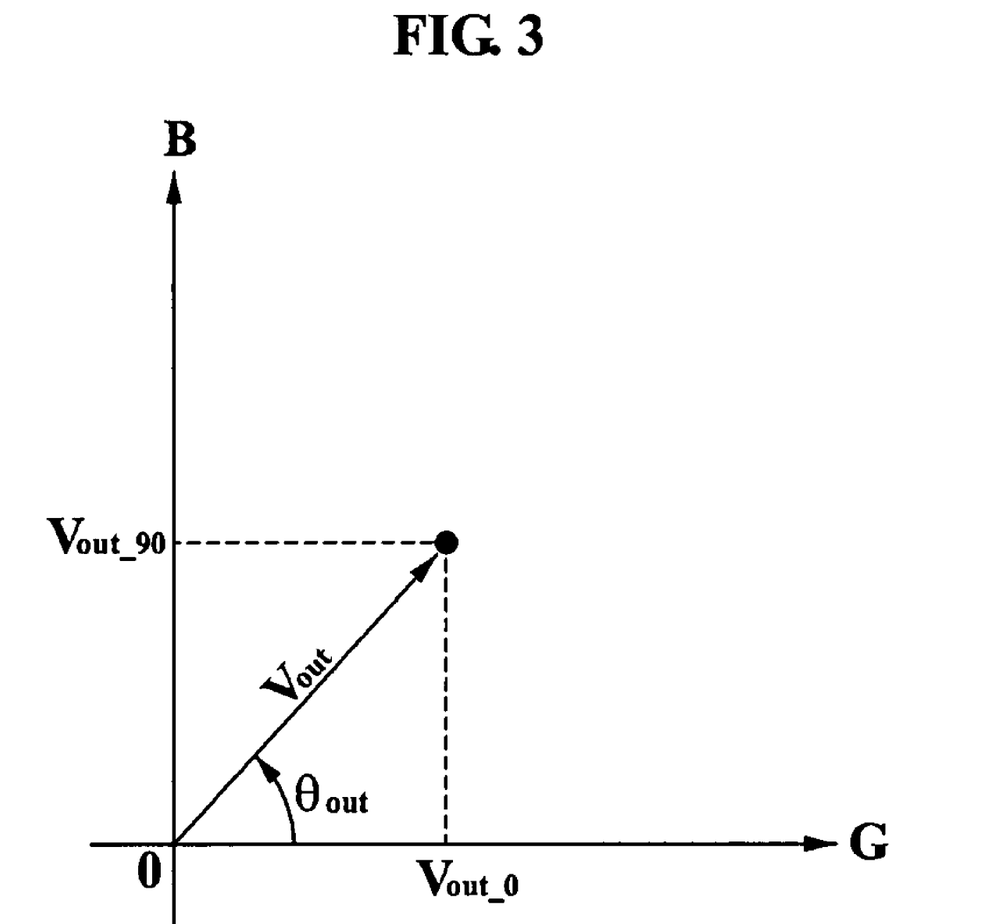
FIG. 3 is a diagram illustrating a graph of an admittance by a skin moisture content measurement result.

FIG. 3 is a diagram illustrating a graph of an admittance by a skin moisture content measurement result.

To electrically measure the skin moisture content, it is required to electrically model the biological structure of the skin. FIG. 1 illustrates an electrically modeled biological structure of skin as widely used in the art.

In FIG. 1, $G_{DC}$ generally indicates a sweat gland activity of a stratum corneum. $R_\infty$ indicates a value which is acquired by electrically modeling a liable cell from a bottom of a stratum corneum to a dermis. The $R_\infty$ is direct current (DC) dominant, $Y_{POL}$ indicates an admittance component due to a polarizing phenomenon, $Gp_{POL}$ indicates a conductance component due to a polarizing phenomenon, and is alternating current (AC) dominant. A $\omega C_{POL}$ component is known to model the skin moisture content of the stratum corneum. Accordingly, when measuring the skin moisture content of the stratum corneum, removing an effect of the $R_\infty$ and the $G_{DC}$ may become an important issue.

To measure only the $\omega C_{POL}$ component, only susceptance which is an AC component of the admittance component is required to be measured. For this, an analog lock-in amplifier may be utilized.

Specifically, the $R_\infty$ may be assumed to be a conductor as shown in FIG. 2. When a constant voltage signal of a regular frequency, for example, $\omega=2\pi f$, is supplied to a human body by using the $R_\infty$ as the conductor, a current, which reacts to an impedance of the stratum corneum, may be measured through the conductor of a liable cell layer. In this instance, the stratum corneum closely attaches to a measurement electrode. The admittance of the stratum corneum of a measured area may be measured by using the current.

A response signal which converts the measured current to a voltage is represented below in Equation 1, where Vsig denotes a measured signal voltage, $\omega$ denotes $2\pi f$ (f being an input signal frequency), r denotes resistance, t denotes time, and $\theta$ sig denotes a phase difference of a response signal:

$$Vsig = |Vsig|\sin(\omega rt + \theta sig) \qquad \text{[Equation 1]}$$

Also, an out-of-phase reference signal having a phase difference of 90° to be synchronous with the response signal is represented below in Equation 2, where $V_{L\_90}$ denotes an out-of-phase reference signal, $\omega_{L\_90t}$ denotes an out-of-phase signal frequency, and $\theta_{ref\_90}$ denotes an out-of-phase signal phase difference:

$$V_{L\_90} = |V_{L\_90}|\cos(\omega_{L\_90t} + \theta_{ref\_90}) \qquad \text{[Equation 2]}$$

In this case, an in-phase reference signal having a phase difference of 0° to be synchronous with the response signal may be represented below in Equation 3, where $V_{L\_0}$ denotes an in-phase reference signal, $\omega_{L\_0t}$ denotes an in-phase reference frequency, and $\theta_{ref\_0}$ denotes an in-phase reference phase difference:

$$V_{L\_O} = |V_{L\_0}|\sin(\omega_{L\_0t} + \theta_{ref\_0}) \qquad \text{[Equation 3]}$$

In this instance, when synchronizing the response signal and the reference signal having the phase difference of 90° using a multiplier, a signal may be generated as shown below in Equation 4, where $\omega$ denotes $2\pi f$ (f being an input signal frequency), r denotes resistance, t denotes time, $\omega_{L\_90}$ denotes an out-of-phase signal frequency, and $\theta_{ref\_90}$ denotes an out-of-phase signal phase difference:

$$\begin{aligned}V_{PSD} = &|Vsig||V_{L\_90}|\sin(\omega rt + \theta sig)\cos(\omega L\_90t + \theta_{ref\_90}) = \\ &1/2|Vsig||V_{L\_90}|\{\sin([\omega r - \omega_{L\_90}]t + \theta sig - \theta_{ref\_90}) - \\ &\sin([\omega r + \omega_{L\_90}]t + \theta sig + \theta_{ref\_90})\}\end{aligned} \qquad \text{[Equation 4]}$$

Also, when the signal passes through a low-pass filter (LPF), the AC component is removed from the signal. Accordingly, $V_{PSD}$ becomes '0'.

However, when frequencies of the reference signal and the response signal are identical, i.e. $\omega r=\omega_{L\_90}$, an output of the LPF may be represented as shown below in Equation 5, where Vsig denotes a measured signal voltage, $V_{L\_90}$ denotes an out-of-phase reference signal, $\theta$ sig denotes a phase difference of a response signal, and $\theta_{ref\_90}$ denotes an out-of-phase signal phase difference:

$$\text{Vout}\_90 = 1/2|Vsig||V_{L\_90}|\sin(\theta sig - \theta_{ref\_90}) \qquad \text{[Equation 5]}$$

Also, when synchronizing the in-phase reference signal and the response signal by a method as described above, it may be given as shown below in Equation 6, where Vsig denotes a measured signal voltage, $V_{L\_0}$ denotes an in-phase reference signal, $\theta$ sig denotes a phase difference of a response signal, and $\theta_{ref\_90}$ denotes an out-of-phase signal phase difference:

$$\text{Vout\_0} = 1/2|Vsig||V_{L\_0}|\cos(\theta sig - \theta_{ref\_0}) \quad \text{[Equation 6]}$$

Also, when $|VSig||V_L|$=Vout and θ sig−θref=θout to simplify the equations with respect to the Vout_90 and Vout_0, it may be arranged by $$V_{PSD\_filtered\_0} = \tfrac{1}{2}V\text{out}\cos(\theta\text{out}). \quad \text{[Equation 7]}$$

The equations with respect to the Vout_90 and Vout_0, i.e. Equation 5 and Equation 6 designate a conductivity signal which is generated by supplying a constant AC voltage and measuring the current. Accordingly, the admittance is measured. FIG. 3 illustrates a graph of the admittance. In FIG. 3, G designates conductance, and B designates susceptance. When G and an in-phase synchronous signal are combined, G may be measured. When B and a quadrature-phase synchronous signal are combined, B may be measured.

As described above, the skin moisture content may be measured from susceptance that is measured via an out-of-phase signal. Also, the sweat gland activity may be measured from conductance that is measured via an in-phase signal.

A method of measuring skin moisture content by measuring susceptance and a method of measuring sweat gland activity of skin by measuring conductance have been described with FIGS. 1 through 3, and may be applied as a configuration and operation principle of an apparatus for providing skin care information according to a measurement of skin moisture content according to an exemplary embodiment, which will be described with FIGS. 4 through 6.

Figure 4:
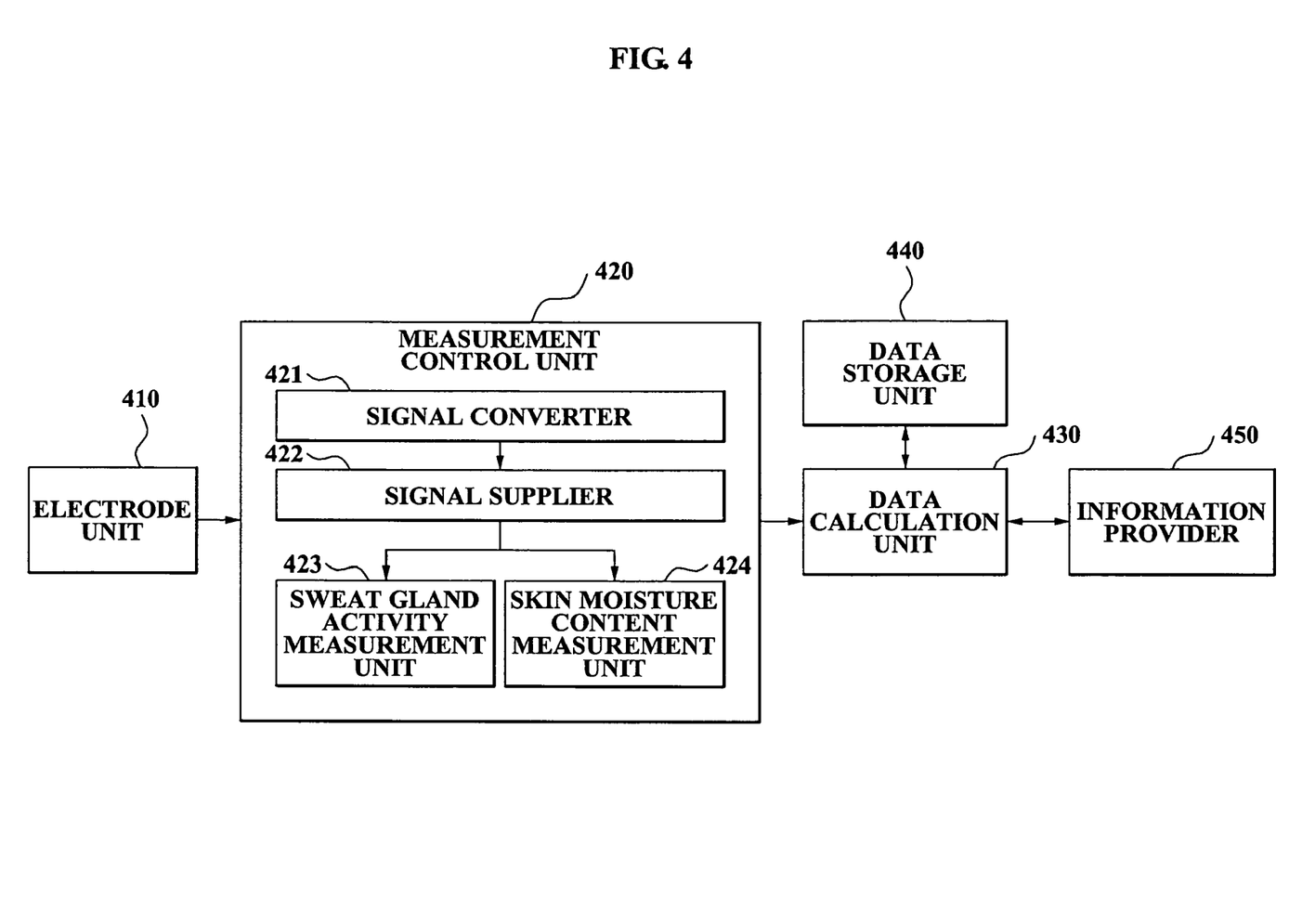
FIG. 4 is a block diagram illustrating a configuration of an apparatus for providing skin care information according to an exemplary embodiment.

FIG. 4 is a block diagram illustrating a configuration of an apparatus for providing skin care information according to an exemplary embodiment.

The apparatus for providing skin care information according to the present exemplary embodiment includes an electrode unit 410, a measurement control unit 420, a data calculation unit 430, a data storage unit 440, and an information provider 450. The electrode unit 410 includes at least one electrode (not illustrated) and a voltage supplier (not illustrated). Also, the measurement control unit 420 includes a signal converter 421, a signal supplier 422, a sweat gland activity measurement unit 423, and a skin moisture content measurement 424.

The electrode unit 410 includes a reference (R) electrode (not illustrated), a measuring (M) electrode (not illustrated), and a current (C) electrode (not illustrated). Specifically, as well-known to those of ordinary skill in the art, the electrode unit may be constructed to include the R electrode, the M electrode, and the C electrode. Also, the electrode unit may be constructed to include any type of electrode that can measure the skin moisture content.

Also, the voltage supplier supplies a voltage to the electrode unit 410. Here, the voltage is supplied to the skin of a user via the R electrode and the C electrode. When the voltage supplied to the skin is influenced by an impedance of a stratum corneum, a current signal may be generated. The M electrode detects the generated current signal, and transmits the detected current signal to the signal converter 421 of the measurement control unit 420, to measure the user's skin moisture content and sweat gland activity.

The signal converter 421 converts the current signal, which is transmitted via the M electrode, into a voltage signal. Also, the signal supplier 422 generates an in-phase signal and an out-of-phase signal with respect to the voltage signal, and supplies the generated in-phase signal and the out-of-phase signal to the voltage signal. Specifically, the signal supplier (not illustrated) generates the out-of-phase signal, which is required to measure susceptance from the voltage signal, and transmits the generated out-of-phase signal to the skin moisture content measurement unit 424. Here, the out-of-phase signal has a phase difference of 90° with the voltage signal, and may be embodied as a cosine wave.

Also, the signal supplier 422 generates the in-phase signal, which is required to measure conductance from the voltage signal, and transmits the generated in-phase signal to the sweat gland activity measurement unit 423. Here, the in-phase signal has a phase difference of 0° with the voltage signal, and may be embodied as a sine wave.

The skin moisture content measurement unit 424 receives the voltage signal from the signal converter 421, and receives the out-of-phase signal from the signal supplier 422. Also, the skin moisture content measurement unit 424 synchronizes the voltage signal and the out-of-phase signal and measures the susceptance of the current signal.

As an example, as described above with FIGS. 1 through 3, the voltage signal may be represented as $$V\text{sig}=|V\text{sig}|\sin(\omega rt+\theta \text{ sig})$$

Also, the out-of-phase signal may be represented as $$V_{L\_90}=|V_{L\_90}|\cos(\omega_{L\_90}t+\theta_{ref\_90})$$

By synchronizing the voltage signal and the out-of-phase signal, the skin moisture content measurement unit 424 may output $$V\text{out\_90}=\tfrac{1}{2}|V\text{sig}||V_{L\_90}|\sin(\theta \text{ sig}-\theta_{ref\_90})$$

Here, since the signal designates a conductivity signal which is generated by supplying a constant AC voltage and measuring the current, the admittance is measured. When representing the signal into a rectangular form, it may be illustrated as the graph of FIG. 3.

In FIG. 3, the graph may be represented as Y=G+iB where Y designates the admittance, G designates the conductance, and B designates the susceptance. Here, when B is synchronized with the out-of-phase signal, B may be measured. Specifically, the skin moisture content measurement unit 424 may measure the susceptance of the current signal by synchronizing the voltage signal and the out-of-phase signal. Also, the skin moisture content measurement unit 424 may output the user's skin moisture content information by using the measured susceptance.

The sweat gland activity measurement unit 423 receives the voltage signal from the signal converter 421, and receives the in-phase signal from the signal supplier 422. Also, the sweat gland activity measurement unit 423 synchronizes the voltage signal and the in-phase signal and measures the conductance of the current signal.

As an example, as described above with FIGS. 1 through 3, the voltage signal may be represented as $$V\text{sig}=|V\text{sig}|\sin(\omega rt+\theta \text{ sig})$$

Also, the in-phase signal may be represented as $$V_{L\_0}=|V_{L\_0}|\sin(\omega_{L\_0}t+\theta_{ref\_0})$$

By synchronizing the voltage signal and the in-phase signal, the sweat gland activity measurement unit 423 may output $$V\text{out\_0}=\tfrac{1}{2}|V\text{sig}||V_{L\_0}|\cos(\theta \text{ sig}-\theta_{ref\_0})$$

Here, since the signal designates a conductivity signal which is generated by supplying the constant AC voltage and measuring the current, the admittance is measured. When representing the signal into a rectangular form, it may be illustrated as the graph of FIG. 3.

As described above, the graph of FIG. 3 may be represented as Y=G+iB. Here, when C is synchronized with the in-phase signal, C may be measured. Specifically, the sweat gland activity measurement unit 423 may measure the conductance of the current signal by synchronizing the voltage signal and the in-phase signal. Also, the sweat gland activity measurement unit 423 may output the user's sweat gland activity information by using the measured conductance.

As described above, the user's skin moisture content and sweat gland activity may be simultaneously measured by measuring the susceptance and the conductance of the current signal that is detected from the user skin, supplied with the voltage, via the M electrode (not illustrated). The measurement control unit 420 transmits the skin moisture content information and the sweat gland activity information to the data calculation unit 430.

The data calculation unit 430 calculates a correlation between the skin moisture content and the sweat gland activity, derives skin moisture content information, and generates skin care information corresponding to the skin moisture content information. Here, the correlation between the skin moisture content and the sweat gland activity may be calculated depending upon whether the sweat gland activity is within a range of a predetermined normal sweat gland activity. In this instance, the range of the normal sweat gland activity may be set to an average of sweat gland activities which are measured with respect to physically and mentally stable general users in an environment where a desirable room temperature is maintained. However, exemplary embodiments are not limited thereto and thus the range of the normal sweat gland activity may be set by using various types of methods depending upon judgments of those skilled in the art.

When the sweat gland activity is within the range of the normal sweat gland activity, the data calculation unit 430 determines the measured skin moisture content is normally measured without any effect from sweat glands and thus, finally determines the measured skin moisture content as the user's skin moisture content information.

Also, the data calculation unit 430 generates skin care information corresponding to the skin moisture content information. In this instance, the skin care information may be embodied into various types of information that includes the skin moisture content information depending upon judgments of those skilled in the art, to help the user's skin care or skin beauty.

Also, the data calculation unit 430 transmits the skin moisture content information and the skin care information to the information provider 450. Here, the information provider 450 may be embodied into a device which can input/output image information or audio information, such as a display device, a voice information providing apparatus, and the like.

Also, the data calculation unit 430 may transmit the sweat gland activity, the skin moisture content, and the skin moisture content information to the data storage unit 440. The data storage unit 440 stores the sweat gland activity, the skin moisture content, the skin moisture content information, the skin care information, and the like, which are received from the data calculation unit 430. In this instance, the stored information may be utilized to compare a tendency of the skin moisture content information of the user over time, or may be utilized to compare the skin moisture content information, and the like, among a plurality of users in a specific situation.

Conversely, when the sweat gland activity is outside the range of the normal sweat gland activity, the data calculation unit 430 may determine the user is in an undesirable environment for measuring skin moisture content, and transmits a measurement environment checklist to the information provider 450 so that the user may measure the skin moisture content in the desirable environment.

In this instance, the undesirable environment for measuring the skin moisture content may include internal or external environmental elements, such as when the user measures the skin moisture content immediately after performing a physically strenuous activity and becoming sweaty, when the user measures the skin moisture content in a mentally unstable state, when the user measures the skin moisture content immediately after having spicy food or drinking a large amount of caffeinated beverages, when a temperature and a humidity is high or low, and the like. However, exemplary embodiments are not limited thereto.

The information provider 450 provides the user with the measurement environment checklist transmitted from the data calculation unit 430. The user inputs information about any undesirable environment the user is currently under in the provided measurement environment checklist. The data calculation unit 430 receives the information from the information provider 450, compares the received information with a desirable measurement environment which is stored in a measurement environment database (not illustrated), and then determines the undesirable environment the user is currently under depending upon a result of the comparison. Also, the data calculation unit 430 extracts information about matters that require the user's attention from the desirable measurement environment database, and transmits the extracted information to the information provider 450, so that the user may correct the undesirable environment the user is currently under.

The information provider 450 provides the user with the desirable measurement environment information which is received from the data calculation unit 430, and calls the user's attention to the desirable measurement environment information so that the user may re-adjust and stabilize the environment before measuring the skin moisture content. Specifically, the information provider 450 may provide the user with the measurement environment checklist, receive, from the user, measurement environment information corresponding to the measurement environment checklist, read the measurement environment information, and provide the user with user measurement error information depending upon the read environment information, to induce the user to re-measure the skin moisture content and the sweat gland activity.

As described above, according to an exemplary embodiment, an apparatus for providing skin care information may measure skin moisture content which reflects a sweat gland activity, and thereby provide a user with more accurate skin care information.

Also, according to another exemplary embodiment, an apparatus for providing skin care information may calculate a user's stress level by using a sweat gland activity, and provide the user with second skin care information based on the stress level and a level of skin moisture content.

In order to generate the second skin care information, the measurement control unit 420 measures a second sweat gland activity in the user skin applied with a predetermined external stimulus. The external stimulus may be applied to the user skin by the information provider 450. As an example, the information provider 450 may apply the external stress including light or sound to the user skin, to cause the stress.

The data calculation unit 430 may calculate the user's stress level with respect to the external stimulus by using the sweat gland activity. Specifically, the user's stress level may be derived from the second sweat gland activity in the user skin, which occurs due to the external stimulus. A method of deriving the stress level may include various types of well-know methods in the art.

Also, stress may generally cause a bad effect for a skin protection function. In this instance, stress may indicate an intrinsic or extrinsic effect which can destroy individual homeostasis. Generally, mental stress indicates stress. In an aspect of dermatology, atopy, psoriasis, and the like, are related with stress, which results in skin problems. Specifically, stress inhibits skin recovery and thereby causes an impairment in a skin protection function, which results in weakening the skin. Accordingly, when measuring a skin moisture content and a stress level corresponding to a basic standard of the skin protection function, it is possible to more accurately understand a state of the skin protection function and provide a user with more effective skin care information based on the state.

For the above operation, the data calculation unit 430 may calculate the stress level as either a high level or a normal level by using a predetermined stress threshold value. Specifically, when the stress level is greater than or equal to the stress threshold value, the data calculation unit 430 may calculate the stress level as the high level. Conversely, when the stress level is less than the stress threshold value, the data calculation unit 430 may calculate the stress level as the normal value. Also, the data calculation unit 430 may calculate a level of the skin moisture content as either a low level or a normal level by using a predetermined skin moisture content threshold value according to the above-described principle.

The data calculation unit 430 generates second skin care information by using the calculated stress level and the level of the skin moisture content. In this instance, the second skin care information may include other information based on the stress level and the level of the skin moisture content.

As an example, when the stress level is calculated as the high level and the level of the skin moisture content is calculated as the low level, the data calculation unit 430 may generate second skin care information including skin trouble warning information caused by the stress. Specifically, the data calculation unit 430 may determine stress causes an impairment in a skin protection function and thereby may generate the second skin care information which induces the user to take rest and supply the user skin with a sufficient amount of hydration.

Also, when the stress level is calculated as the high level and the level of the skin moisture content is calculated as the normal level, the data calculation unit 430 may generate the second skin care information, including skin trouble warning information caused by the stress. Specifically, the data calculation unit 430 may determine stress exists but hydration is still being stably supplied and thereby may generate the second skin care information which includes warning information about a possibility of skin trouble.

Also, when the stress level is calculated as the normal level and the level of the skin moisture content is calculated as the low level, the data calculation unit 430 may generate the second skin care information, including dehydration information caused by a surrounding environment. Specifically, the data calculation unit 430 may determine dehydration occurs due to the surrounding environment or other elements and thereby may generate the second skin care information which includes information about environment improvement and notice of dermatological problems.

Also, when the stress level is calculated as the normal level and the level of the skin moisture content is calculated as the normal level, the data calculation unit 430 may generate the second skin care information, including current state maintenance information. Specifically, since the user skin currently holds a sufficient amount of hydration, the data calculation unit 430 may generate the second skin care information which includes information about maintaining the current state.

When the data calculation unit 430 generates the second skin care information by using the stress level and the level of skin moisture content, the information provider 450 provides the user with the second skin care information. Also, the second skin care information may be stored in the data storage unit 440.

Figure 5:
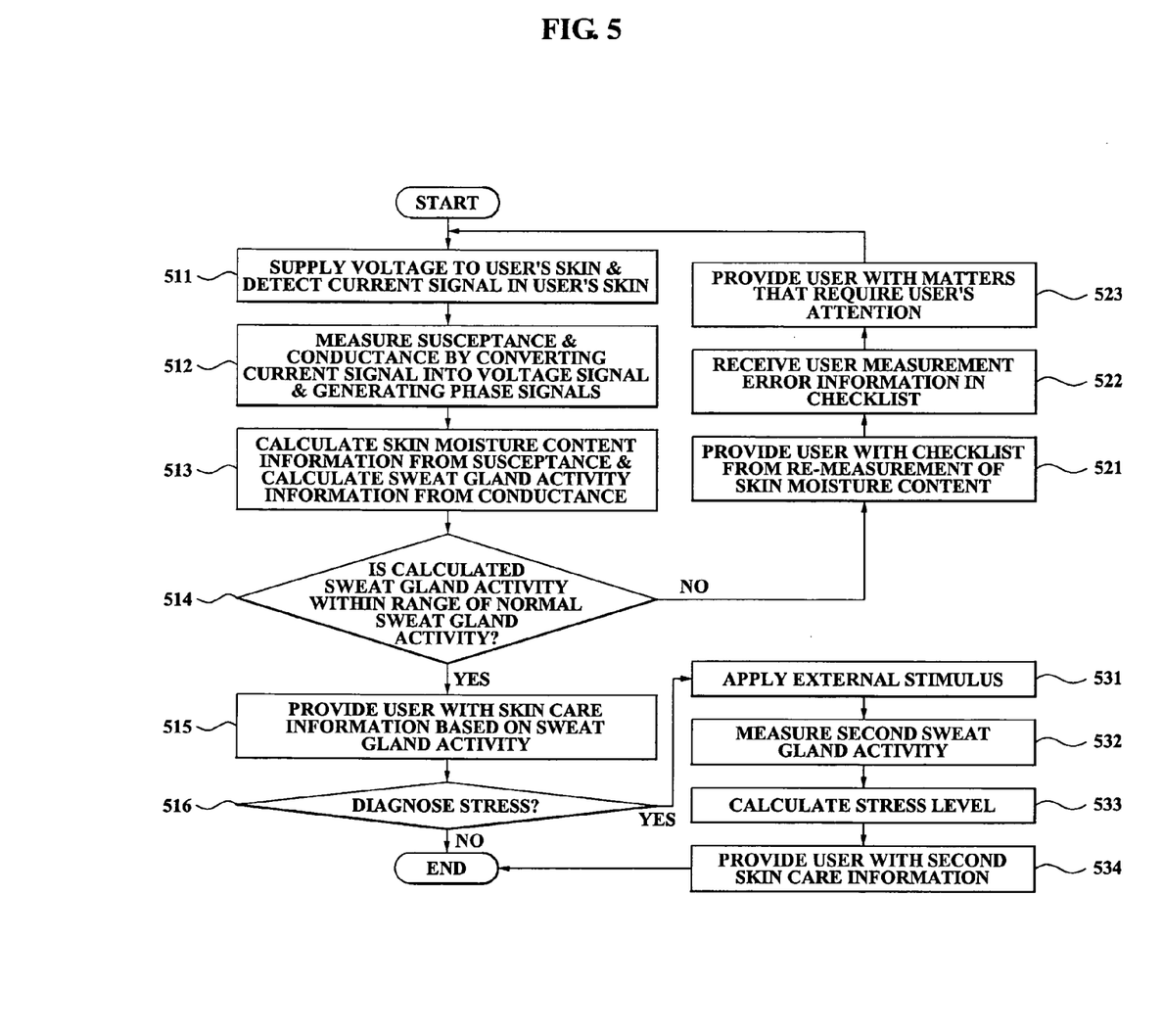
FIG. 5 is a flowchart illustrating a method of providing skin care information according to an exemplary embodiment.

FIG. 5 is a flowchart illustrating a method of providing skin care information according to an exemplary embodiment.

In operation 511, to measure a user's skin moisture content information and sweat gland activity information, an apparatus for providing skin care information according to the present exemplary embodiment supplies a voltage to the user's skin, and detects a current signal in the user's skin.

In operation 512, the apparatus for providing skin care information measures conductance of the current signal by converting the current signal into a voltage signal, generating an in-phase signal and an out-of-phase signal with respect to the voltage signal, and supplying the generated in-phase signal and the out-of-phase signal to the voltage signal, and synchronizing the voltage signal and the in-phase signal. Also, in operation 512, the apparatus for providing skin care information measures susceptance of the current signal by synchronizing the voltage signal and the out-of-phase signal.

In operation 513, the apparatus for providing skin care information calculates the user's sweat gland activity information from the measured conductance, and calculates the user's skin moisture content information from the measured susceptance.

In operation 514, the apparatus for providing skin care information determines whether the calculated sweat gland activity is within a range of a predetermined normal sweat gland activity, and finally determines the skin moisture content as the user's skin moisture content information when the calculated sweat gland activity is within the range of the normal sweat gland activity.

In operation 515, the apparatus for providing skin care information generates skin care information corresponding to the skin moisture content information and provides the user with the generated skin care information.

In this instance, the range of the normal sweat gland activity may be set to an average of sweat gland activities which are measured with respect to physically and mentally stable general users in an environment where a desirable room temperature is maintained. Also, the skin care information may be embodied into various types of information that includes the skin moisture content information depending upon judgments of those skilled in the art, to help the user's skin care or skin beauty.

Conversely, when the calculated sweat gland activity is outside the range of the normal sweat gland activity in operation 514, the apparatus for providing skin care information determines the user did not measure the skin moisture content information in a desirable skin moisture content measurement environment, and provides the user with a measurement environment checklist so that the user may check the skin moisture content measurement environment in operation 521.

In operation 522, the apparatus for providing skin care information receives information about an undesirable environment the user is currently under in the provided measurement environment checklist.

In operation 523, the apparatus for providing skin care information compares the received information and the desirable measurement environment which is stored in a desirable measurement environment database (not illustrated), and thereby determines the undesirable environment of the user. Also, the apparatus for providing skin care information extracts information about matters that require the user's attention from the desirable measurement environment database, provides the user with the extracted information, and calls the user's attention to the desirable measurement environment information so that the user to may re-adjust and stabilize the environment before measuring the skin moisture content. Specifically, in operation 523, the apparatus inquires whether the user will re-measure the skin moisture content.

In this instance, when the user requests the re-measurement of the skin moisture content, the apparatus for providing skin care information may repeat operations 511 through 514.

In operation 516 after providing the skin care information, the apparatus for providing skin care information inquires whether the user will diagnose stress. In operation 531, when the user selects to diagnose the stress in operation 516, the apparatus applies an external stimulus to the user skin. In this instance, the external stimulus includes light or sound causing stress.

In operation 532, the apparatus for providing skin care information measures a second sweat gland activity in the user skin when the external stimulus is applied to the user skin.

In operation 533, the apparatus for providing skin care information calculates the user's stress level with respect to the external stimulus by using the second sweat gland activity. In this instance, the stress level may be calculated as either a high level or a normal level based on a predetermined stress threshold value. Also, in operation 533, the apparatus for providing skin care information calculates a level of skin moisture content by using the skin moisture content. In this instance, the level of the skin moisture content may be calculated as either a low level or a normal level.

In operation 534, the apparatus for providing skin care information generates second skin care information by using the stress level and the level of the skin moisture content and provides the generated second skin care information.

In operation 534, when the stress level is calculated as the high level and the level of the skin moisture content is calculated as the low level, the apparatus for providing skin care information may generate second skin care information including skin trouble warning information caused by the stress. Specifically, the apparatus for providing skin care information may determine stress causes an impairment in a skin protection function and thereby may generate the second skin care information which induces the user to rest and supply the user skin with a sufficient amount of hydration.

Also, in operation 534, when the stress level is calculated as the high level and the level of the skin moisture content is calculated as the normal level, the apparatus for providing skin care information may generate the second skin care information, including skin trouble warning information caused by the stress. Specifically, the apparatus for providing skin care information may determine stress exists but hydration is still stably being supplied and thereby may generate the second skin care information which includes warning information about a possibility of skin trouble.

Also, in operation 534, when the stress level is calculated as the normal level and the level of the skin moisture content is calculated as the low level, the apparatus for providing skin care information may generate the second skin care information, including dehydration information caused by a surrounding environment. Specifically, the apparatus for providing skin care information may determine dehydration occurs due to the surrounding environment or other elements and thereby may generate the second skin care information which includes information about environment improvement and notice of dermatological problems.

Also, in operation 534, when the stress level is calculated as the normal level, and the level of the skin moisture content is calculated as the normal level, the apparatus for providing skin care information may generate the second skin care information, including current state maintenance information. Specifically, since the user skin currently holds a sufficient amount of hydration, the apparatus for providing skin care information may generate the second skin care information which includes information about maintaining the current state.

The apparatus for providing skin care information may provide the second skin care information for a user on a display, an audio, and the like.

In addition to the above-described exemplary embodiments, embodiments can also be implemented by executing computer readable code/instructions in/on a medium/media, e.g., a computer readable medium/media. The medium/media can correspond to any medium/media permitting the storing of the computer readable code/instructions. The medium/media may also include, alone or in combination with the computer readable code/instructions, data files, data structures, and the like. Examples of code/instructions include both machine code, such as produced by a compiler, and files containing higher level code that may be executed by a computing device and the like using an interpreter. In addition, code/instructions may include functional programs and code segments.

The computer readable code/instructions can be recorded on a medium/media in a variety of ways, with examples of the medium/media including magnetic storage media (e.g., floppy disks, hard disks, magnetic tapes, etc.), optical media (e.g., CD-ROMs, DVDs, etc.), magneto-optical media (e.g., floptical disks), and hardware storage devices (e.g., read only memory media, random access memory media, flash memories, etc.). The medium/media may also be a distributed network, so that the computer readable code/instructions are stored and executed in a distributed fashion. The computer readable code/instructions may be executed by one or more processors. The computer readable code/instructions may also be executed and/or embodied in at least one application specific integrated circuit (ASIC) or Field Programmable Gate Array (FPGA).

In addition, one or more software modules or one or more hardware modules may be configured in order to perform the operations of the above-described exemplary embodiments.

The term "module", as used herein, denotes, but is not limited to, a software component, a hardware component, a plurality of software components, a plurality of hardware components, a combination of a software component and a hardware component, a combination of a plurality of software components and a hardware component, a combination of a software component and a plurality of hardware components, or a combination of a plurality of software components and a plurality of hardware components, which performs certain tasks. A module may advantageously be configured to reside on the addressable storage medium/media and configured to execute on one or more processors. Thus, a module may include, by way of example, components, such as software components, application specific software components, object-oriented software components, class components and task components, processes, functions, operations, execution threads, attributes, procedures, subroutines, segments of program code, drivers, firmware, microcode, circuitry, data, databases, data structures, tables, arrays, and variables. The functionality provided for in the components or modules may be combined into fewer components or modules or may be further separated into additional components or modules. Further, the components or modules can operate at least one processor (e.g. central processing unit (CPU)) provided in a device. In addition, examples of a hardware components include an application specific integrated circuit (ASIC) and Field Programmable Gate Array (FPGA). As indicated above, a module can also denote a combination of a software component(s) and a hardware component(s). These hardware components may also be one or more processors.

The computer readable code/instructions and computer readable medium/media may be those specially designed and constructed for the purposes of embodiments, or they may be of the kind well-known and available to those skilled in the art of computer hardware and/or computer software.

According to above-described exemplary embodiments, a method, apparatus, and medium for providing skin care information may simultaneously measure skin moisture content and a sweat gland activity in a stratum corneum, and thereby can provide a user with skin care information and skin moisture content information based on the measured sweat gland activity.

Also, according to above-described exemplary embodiments, a method, apparatus, and medium for providing skin care information may measure a user's sweat gland activity in the user skin when an external stimulus is applied to the user skin, calculate the user's stress level, generate skin care information based on the user's stress by using the stress level and skin moisture content, and thereby provide the generated skin care information.

Although a few exemplary embodiments have been shown and described, it would be appreciated by those skilled in the art that changes may be made in these exemplary embodiments, and the scope of embodiments are defined in the claims and their equivalents.

What is claimed is:

1. An apparatus for providing skin care information, the apparatus comprising:
    an electrode unit adapted to supply a voltage to a user's skin and to detect a current signal in the user's skin, wherein the electrode unit comprises an M electrode;
    a measurement control unit to measure the user's skin moisture content and sweat gland activity by using the detected current signal;
    a data calculation unit to derive skin moisture content information by using calculation of interrelation between the skin moisture content and the sweat gland activity, and to generate skin care information corresponding to the skin moisture content information; and
    an information provider to provide the user with the generated skin care information, wherein the measurement control unit comprises:
    a signal converter to convert the current signal into a voltage signal;
    a signal supplier to generate an in-phase signal and an out-of-phase signal with respect to the voltage signal, and supplying the generated in-phase signal and the out-of-phase signal to the voltage signal;
    a sweat gland activity measurement unit to measure conductance of the current signal by synchronizing the voltage signal and the in-phase signal, and measuring the sweat gland activity of the user's skin from the measured conductance of the current signal; and
    a skin moisture content measurement unit to measure susceptance of the current signal by synchronizing the voltage signal and the out-of-phase signal, and measuring the skin moisture content of the user's skin from the measured susceptance of the current signal,
    wherein the susceptance and conductance of the current signal that is detected from the user's skin, supplied with the voltage, by way of the M electrode is used to simultaneously measure skin moisture content and sweat gland activity,
    wherein the data calculation unit determines whether the sweat gland activity is within a range of a predetermined normal sweat gland activity and when the measured sweat gland activity is within the range of the normal sweat gland activity, the data calculating unit determines that the measured skin moisture content is normally measured without any effect from sweat glands, thereby deriving the skin moisture content information, and
    wherein the data calculation unit determines the user did not measure the skin moisture content information in a desirable skin moisture content measurement environment and the data calculation unit controls the information provider to provide the user with a measurement environment checklist when the measured sweat gland activity is outside the range of the normal sweat gland activity.

2. The apparatus of claim 1, further comprising:
    a data storage unit to store the skin care information or the skin moisture content information.

3. The apparatus of claim 1, wherein the data calculation unit derives the measured skin moisture content as the user's skin moisture content information when the measured sweat gland activity is within the range of the normal sweat gland activity.

4. The apparatus of claim 1, wherein the information provider provides the user with the measurement environment checklist, receives, from the user, measurement environment information corresponding to the measurement environment checklist, reads the measurement environment information, and provides the user with user measurement error information depending upon the read environment information, to induce the user to re-measure the skin moisture content and the sweat gland activity.

5. The apparatus of claim 1, wherein:
    the measurement control unit measures a second sweat gland activity in the user's skin being applied with a predetermined external stimulus,
    the data calculation unit calculates the user's stress level with respect to the external stimulus by using the second sweat gland activity, and generates second skin care information by using the stress level and the skin moisture content, and
    the information provider provides the user with the second skin care information.

6. The apparatus of claim 5, wherein the information provider applies the external stimulus to the user, the external stimulus including light or sound causing stress to the user's skin.

7. The apparatus of claim 5, wherein the data calculation unit calculates the stress level as either a high level or a normal level by using a predetermined stress threshold value, and calculates a level of the skin moisture content as either a low level or a normal level by using a predetermined skin moisture content threshold value.

8. The apparatus of claim 7, wherein the data calculation unit generates the second skin care information, including skin trouble warning information caused by the stress, when the stress level is calculated as the high level and the level of the skin moisture content is calculated as the low level.

9. The apparatus of claim 7, wherein the data calculation unit generates the second skin care information, including skin trouble warning information caused by the stress, when the stress level is calculated as the high level and the level of the skin moisture content is calculated as the normal level.

10. The apparatus of claim 7, wherein the data calculation unit generates the second skin care information, including dehydration information caused by a surrounding environment, when the stress level is calculated as the normal level and the level of the skin moisture content is calculated as the low level.

11. The apparatus of claim 7, wherein the data calculation unit generates the second skin care information, including current state maintenance information, when the stress level is calculated as the normal level and the level of the skin moisture content is calculated as the normal level.

12. The apparatus of claim 1, wherein the range of the normal sweat gland activity is set based on an average of sweat gland activities which are measured with respect to a plurality of physically and mentally stable general users in an environment where a desirable room temperature is maintained.

13. A method for providing skin care information, the method comprising:
supplying a voltage to a user's skin using an M electrode, and detecting a current signal in the user's skin using an M electrode;
measuring the user's skin moisture content and sweat gland activity by using the current signal,
deriving skin moisture content information by using the skin moisture content and the sweat gland activity;
generating skin care information corresponding to the skin moisture content information using at least one processor; and
providing the user with the generated skin care information,
wherein a measurement control unit measures the user's skin moisture content and sweat gland activity by using the current signal,
wherein the measurement control unit comprises:
a signal converter to convert the current signal into a voltage signal;
a signal supplier to generate an in-phase signal and an out-of-phase signal with respect to the voltage signal, and supplying the generated in-phase signal and the out-of-phase signal to the voltage signal;
a sweat gland activity measurement unit to measure conductance of the current signal by synchronizing the voltage signal and the in-phase signal, and measuring the sweat gland activity of the user's skin from the measured conductance of the current signal; and
a skin moisture content measurement unit to measure susceptance of the current signal by synchronizing the voltage signal and the out-of-phase signal, and measuring the skin moisture content of the user's skin from the measured susceptance of the current signal,
wherein the susceptance and conductance of the current signal that is detected from the user's skin, supplied with the voltage, by way of the M electrode is used to simultaneously measure skin moisture content and sweat gland activity,
wherein the deriving comprises determining whether the measured sweat gland activity is within a range of a predetermined normal sweat gland activity, determining the measured skin moisture content is normally measured without any effect from sweat glands when the measured sweat gland activity is within the range of the normal sweat gland activity, and deriving the measured skin moisture content as the user's skin moisture content information, and
wherein the deriving further comprises determining the user did not measure the skin moisture content information in a desirable skin moisture content measurement environment, and providing the user with the measurement environment checklist, receiving, from the user, measurement environment information corresponding to the measurement environment checklist, reading the measurement environment information, and providing the user with user measurement error information depending upon the read environment information, to induce the user to re-measure the skin moisture content and the sweat gland activity, when the measured sweat gland activity is outside the range of the normal sweat gland activity.

14. The method of claim 13, further comprising:
storing either the skin care information or the skin moisture content information.

15. The method of claim 13, further comprising:
measuring a second sweat gland activity in the user's skin being applied with a predetermined external stimulus,
calculating the user's stress level with respect to the external stimulus by using the second sweat gland activity;
generating second skin care information by using the stress level and the skin moisture content; and
providing the user with the second skin care information.

16. The method of claim 15, wherein the measuring of the second sweat gland activity comprises:
applying the external stimulus to the user, the external stimulus including light or sound causing stress to user's skin.

17. The method of claim 15, wherein the stress level is calculated as either a high level or a normal level based on a predetermined stress threshold value, and a level of the skin moisture content is calculated as either a low level or a normal level based on a predetermined skin moisture content threshold value.

18. The method of claim 17, wherein the generating of the second skin care information comprises:
generating the second skin care information, including skin trouble warning information caused by the stress, when the stress level is calculated as the high level and the level of the skin moisture content is calculated as the low level;
generating the second skin care information, including skin trouble warning information caused by the stress, when the stress level is calculated as the high level and the level of the skin moisture content is calculated as the normal level;
generating the second skin care information, including dehydration information caused by a surrounding environment, when the stress level is calculated as the normal level and the level of the skin moisture content is calculated as the low level; and
generating the second skin care information, including current state maintenance information, when the stress level is calculated as the normal level and the level of the skin moisture content is calculated as the normal level.

19. The method of claim 13, wherein the range of the normal sweat gland activity is set based on an average of sweat gland activities which are measured with respect to a plurality of physically and mentally stable general users in an environment where a desirable room temperature is maintained.

20. At least one non-transitory computer readable medium storing computer readable instructions that control at least one processor to implement a method for providing skin care information, the method comprising:
  supplying a voltage to a user's skin using an M electrode, and detecting a current signal in the user's skin using an M electrode;
  measuring the user's skin moisture content and sweat gland activity by using the current signal;
  deriving skin moisture content information by using the skin moisture content and the sweat gland activity;
  generating skin care information corresponding to the skin moisture content information; and
  providing the user with the generated skin care information,
  wherein a measurement control unit measures the user's skin moisture content and sweat gland activity by using the current signal,
  wherein the measurement control unit comprises:
  a signal converter to convert the current signal into a voltage signal;
  a signal supplier to generate an in-phase signal and an out-of-phase signal with respect to the voltage signal, and supplying the generated in-phase signal and the out-of-phase signal to the voltage signal;
  a sweat gland activity measurement unit to measure conductance of the current signal by synchronizing the voltage signal and the in-phase signal, and measuring the sweat gland activity of the user's skin from the measured conductance of the current signal; and
  a skin moisture content measurement unit to measure susceptance of the current signal by synchronizing the voltage signal and the out-of-phase signal, and measuring the skin moisture content of the user's skin from the measured susceptance of the current signal,
  wherein the susceptance and conductance of the current signal that is detected from the user's skin, supplied with the voltage, by way of the M electrode is used to simultaneously measure skin moisture content and sweat gland activity,
  wherein the deriving comprises determining whether the measured sweat gland activity is within a range of a predetermined normal sweat gland activity, determining the measured skin moisture content is normally measured without any effect from sweat glands when the measured sweat gland activity is within the range of the normal sweat gland activity, and deriving the measured skin moisture content as the user's skin moisture content information, and
  wherein the deriving further comprises determining the user did not measure the skin moisture content information in a desirable skin moisture content measurement environment, and providing the user with the measurement environment checklist, receiving, from the user, measurement environment information corresponding to the measurement environment checklist, reading the measurement environment information, and providing the user with user measurement error information depending upon the read environment information, to induce the user to re-measure the skin moisture content and the sweat gland activity, when the measured sweat gland activity is outside the range of the normal sweat gland activity.

21. The at least one non-transitory computer readable medium as recited in claim 20, wherein the range of the normal sweat gland activity is set based on an average of sweat gland activities which are measured with respect to a plurality of physically and mentally stable general users in an environment where a desirable room temperature is maintained.

* * * * *